United States Patent [19]
Orgel et al.

[11] Patent Number: 4,865,968
[45] Date of Patent: Sep. 12, 1989

[54] DNA SEQUENCING

[75] Inventors: Leslie E. Orgel, LaJolla; James W. Patrick, Solana Beach, both of Calif.

[73] Assignee: The Salk Institute for Biological Studies, San Diego, Calif.

[21] Appl. No.: 718,724

[22] Filed: Apr. 10, 1985

[51] Int. Cl.[4] .................... C12Q 1/68; G01N 27/26; G01N 21/63

[52] U.S. Cl. .................... 435/6; 435/803; 935/77; 204/182.8

[58] Field of Search ............. 435/6, 91, 803; 204/403, 182.8; 436/501; 935/77, 78

[56] References Cited

FOREIGN PATENT DOCUMENTS 0115777  8/1984  European Pat. Off. ............. 435/6

OTHER PUBLICATIONS

Gray, A. J. et al, *Nucleic Acids Research*, vol. 12, 1984, pp. 473–491.
F. Sanger et al., *Proc. Natl. Acad. Sci USA* 74 5463–5467 (1977).
A. M. Maxam & W. Gilbert, *Proc. Natl. Acad. Sci. USA* 74, 560–564 (1977).
J. Maat & A. J. Smith, *Nucleic Acid Res.* 5, 4537–4540 (1978).
R. Staden, *Nucleic Acids Research* 12, 499–503 (1984).
D'Alessio, J. M., *Gel Electrophoresis of Nucleic Acids*, R. Rickwood & B. D. Hames, eds. IRL Press, Oxford (1983), pp. 173–197.
A. S. Krayev, *FEBS Letters* 130, 19–22 (1981).

*Primary Examiner*—Johnnie R. Brown
*Assistant Examiner*—Jeremy M. Jay
*Attorney, Agent, or Firm*—Fitch, Even, Tabin & Flannery

[57] ABSTRACT

A first mixture is prepared that contains labeled chain fragments which each has a common end adjacent to a primary nucleotide and a termination at a position from the primary through an nth nucleotide, the first mixture containing nucleotide chain fragments of each length from termination at the primary through termination of the nth nucleotide. A second mixture is prepared that contains labeled chain fragments beginning at the common end and terminating at positions from the first through the nth nucleotide, the second mixture containing chain fragments of each length terminating wherever either a first or a second of the four nucleotides occurs. A third mixture is prepared that contains labeled chain fragments beginning at the common end and terminating at a position from the first through the nth nucleotide, the third mixture containing chain fragments of each length terminating wherever the first or a third of the four nucleotide sequences occurs. The chains are electrophoresed with the first mixture as the center lane. This three-lane system provides a unique band pattern for each of the four nucleotides and permits the sequence to be read merely by directly comparing each of the flanking lanes with the fully stepped center lane. This system has important advantages in reducing reading errors, particularly when read with computer-assisted scanning apparatus.

16 Claims, No Drawings

DNA SEQUENCING

The invention was made with Government support under Contract No. DAND-17-82-C-2126 awarded by the Army Medical Research and Development Command. The Government has certain rights in this invention.

BACKGROUND OF THE INVENTION

Until relatively recently, DNA sequencing was a very time-consuming and tedious task. Techniques which greatly simplify DNA sequencing have been reported, including the method of Sanger, F. et al., *Proc. Natl Acad. Sci. U.S.A.* 74, 5463–5467 (1977); Maxam, A. M. & Gilbert, W., *Proc. Natl. Acad. Sci. U.S.A.* 74, 560–564 (1977); and J. Maat & A. J. Smith, *Nucleic Acid Res.* 5, 4537–4545, (1978).

The method described in *Sanger et al., supra.* involves the synthesis of a radioactive complementary copy of a single-stranded target sequence with DNA polymerase, using the directly adjacent annealed strand of a restriction fragment as a primer. Using four separate reaction mixtures, which each contain a different dideoxynucleotide triphosphate (ddNTP) terminator and, in addition, the four deoxynucleoside triphosphates (dNTPs) (one or more of which are alpha-$^{32}$P-labelled), there is a partial incorporation of the terminator into the radioactive elongation products. In a single reaction a size range of labelled oligonucleotides is produced, all with a common 5' end, but with the 3' end terminating at the various sites, throughout the sequence, of the nucleotide to which the terminating ddNTP is analogous. Parallel fractionation by denaturing polyacrylamide gel electrophoresis of the products of the four separate reactions, which each contain, in turn, one of the four ddNTP chain terminators, resolves the oligonucleotides of different sizes. These reveal, in order, the positions of each base, allowing a sequence to be determined.

In the protocol of Maat et al., supra. a 5' $^{32}$P-labelled fragment is incubated in the presence of DNA polymerase I and pancreatic DNAase I in four separate reactions. Each reaction contains all four dNTPs and, in turn, one different ddNTP. The pancreatic DNAase I introduces nicks, the 3' hydroxyls of which serve as priming points for DNA polymerase I. Chain extension then proceeds from the 3' end of every nick, leading to a base-specific chain termination in each reaction. The products of the reactions are fractionated on denaturing polyacrylamide slab gels, resolving the oligonucleotides with the common labelled 5' end.

Although the nicking and subsequent chain extension occurs on both strands, because only one is labelled, a pattern of radioactive bands is produced for only that strand, allowing its sequence to be deduced. Nicking of the fragment by DNAase I does not occur at every residue along its length, but the fact that both deoxy- and dideoxy- NTPs are present in each reaction mixture ensures that chain extension continues through several residues of the same base from the site of the nick. Every residue in the sequence therefore gives rise to a band.

In both Sanger et al. and Maat et al. variations of chain elongation with terminators, four lanes are required to deduce the nucleotide sequence. Each lane defines the position of one of the four nucleotides with the position being determined relative to the bands in each of the other three lanes. All four lanes must be compared at once, and frequently, mental errors occur when reading across the four-lane pattern. Reading of the four-lane pattern may be quite difficult if the gel is bowed, as is frequently the case, or if other gel artifacts occur.

The method of Maxam and Gilbert supra. relies upon chemical reactions which cleave single chain DNA at nucleotide-specific (to the particular base) sites and also upon the fact that cleaved nucleotide chains of different lengths migrate at different rates on polyacrylamide gels. A single chain DNA sequence is tagged, e.g., radioactively, at one end. Then, various aliquots of the tagged chain are subjected to separate reactions mixtures which each cause, on the average, a single cleavage of the chain and at a specific nucleotide or nucleotides, e.g., two of the four. The several aliquots of fragmented chains are then run on side-by-side lanes on a polyacrylamide gel. With a chain of "n" nucleotides (n generally being no greater than 200), the several lanes together provide bands at n distances from the origin; however, as described in Maxam and Gilbert, each lane has only those bands corresponding to the specific cleavage site or sites. The nucleotide corresponding to each band distance from the origin is deduced from the band pattern across the gel, that is, in the direction normal to the migration direction.

Maxam and Gilbert have proposed a four-lane system in which each lane represents a fragmentation at one or two specific nucleotide sites. In one particular embodiment of the Maxam and Gilbert method, the four lanes represent (1) A(adenine) +G (guanine), (2) G (3) C (cytosine) and (4) C + T(thymine). In this sytem, a single band in lane 1 is conclusive of A at the cleavage site; side-by-side bands in lanes 1 and 2 are conclusive of G at the cleavage site, a single band in lane 4 is conclusive of T in this position and side-by-side bands in lanes 3 and 4 are conclusive of C at the cleavage site.

The results are unambiguous, providing that the gel is sufficiently clear; however, as practitioners in the art are well aware, gel resolution is often not of the quality that is desired. Problems with clarity include compressions, artifacts, pile-ups, and ghost bands. Furthermore, the bands in the different lanes do not generally align as straight across as might be desired, frequently being rather bowed. Because of this, reading of gels requires some experience and is still subject to error.

Several techniques are employed to reduce error. One of these is redundancy. Maxam and Gilbert recognize that their four lane system contains more information than is necessary to deduce the sequence and that a three-lane system with each lane representing a single nucleotide cleavage site would provide sufficient information to deduce the sequence; however, they strongly suggest that such redundancy is required to give reliable results. Reading of three lanes exhibiting cleavage at a single site each (or termination at a single site each in the chain elongation procedures, described above) would require judgments of spacing to deduce sites of the fourth nucleotide, which is complicated by the fact that the spacing between bands varies according to the terminal nucleotide. Another way of reducing error is to sequence both the encoding chain and its complementary strand.

While the above-described systems have worked relatively well, greatly reducing the time needed for nucleotide suquencing, there is a demand for even more precise and rapid sequencing. Because the genetic code comprises an arrangement of four nucleotides, and corresponding band patterns across an electrophoretic gel system are, in principle, simple to interpret, the systems lend themselves to automatic sequencing, including interpretation by computers or microprocessors. Interpretation by microprocessors, in addition to saving time, can also be expected to reduce technician mental errors of the type caused by misassignment of bands to lanes, a type of mental error that occurs frequently due to the tedious nature of reading an extended sequence.

While computer means can be substantially errorfree with respect to assigning bands to their proper lanes or other such mental errors, automatic equipment may in many cases be less efficient than a technician in correctly identifying which bands are, in reality, colinear across the gel. Because substantial bowing of bands often exist, it is very difficult for optical scanning apparatus to correctly identify which bands should be considered as having migrated equal distances from the origin. This function may be better performed by a skilled technician who can recognize the curvature in a particular gel pattern and adjust his interpretation accordingly.

Rodger Staden in *Nucleic Acids Research* 12, 499–503 (1984) describes a computer-assisted method for analyzing DNA sequences. In this system, a technician moves his sensing pen along each lane, placing it down at each band location to register the same into a computer. The computer keeps track of the data and analyzes the nucleotide sequence. Even this system produces substantial uncertainty as the system specifically provides for entry of uncertainty codes.

It would be desirable to have a DNA sequencing system that reduces potential errors caused by curvature in the gel. This would permit fully automatic sequencing by optical scanning apparatus assisted by computing means, such as microprocessors.

SUMMARY OF THE INVENTION

Improved DNA sequencing methods are provided which substantially eliminate errors in reading across a gel pattern, such as may result from gel curvature. This allows the gel to be easily read by automatic equipment, including optical scanning means and associated computing means. The methods of the present invention are improvements of several previously described systems which employ several reaction mixtures that each either terminates a DNA strand during chain elongation in a manner such that termination occurs at a specific nucleotide as distributed throughout the chain or selectively cleaves a DNA chain in a manner such that cleavage occurs at a specific nucleotide or specific nucleotides as distributed throughout the chain. In each of these procedures, as previously described, a series of reaction mixtures are formulated for nucleotide chain elongation and termination or cleavage, and the reaction mixtures are appropriately combined to form gel application mixtures. The application mixtures are run side-by-side on a gel that separates the chain fragments according to their lengths, and a distinct band pattern is produced for each of the four nucleotides at the positions on the gel that correlate to each position in the chain where that nucleotide occurs. Whereas in the previous described sequencing techniques, each gel application mixture was specific for either one or two nucleotides and required four lanes for unambiguous readings or for necessary redundancy, the improvement of the present invention provides a first mixture that includes nucleotide chain fragments of every length, which first gel application mixture is to run as the center lane, a second gel application mixture that includes nucleotide chain fragments terminating at the positions of a first and second nucleotide, which second mixture is to run as one of the flanking lanes and a third gel application mixture that includes nucleotide chain fragments terminating at the positions of the first and a third nucleotide, which third mixture is to run as the second flanking lane. An unambiguous interpretation of the gel pattern is readable by comparing only directly adjacent lanes.

DETAILED DESCRIPTION OF THE PREFERRED EMBODIMENTS

In accordance with the invention, nucleotides are sequenced using three chain fragment mixtures which when electrophoresed in three adjacent lanes of a gel provide a band pattern that permits the positions of each of the four nucleotides to be unambiguously read by comparing each flanking lane directly with the center lane. The first mixture contains randomly generated chain fragments corresponding to each chain length as measured from one end, that is, terminating at each position of each of the four nucleotide sites. The second mixture contains randomly generated chain fragments terminating specifically at each chain position of each of a first or a second nucleotide site. The third mixture contains randomly generated chain fragments terminating specifically at each position of either the first or at a third nucleotide site. The three mixtures of chain fragments are run in side-by-side lanes of an electrophoresis gel, such as a polyacrylamide gel, which separates the nucleotide chain fragments according to their size (length) with the first nucleotide chain mixture being placed in the center lane, and the second and third nucleotide chain mixtures in the left and right flanking lanes.

In a chain of n sequenceable nucleotides, the center lane exhibits bands at all n locations (distances from the origin). The flanking lanes exhibit bands only at locations corresponding to the specific nucleotide termination sites. The location of each of the four nucleotides in the chain is identified by a unique band pattern as read across the lanes, i.e., perpendicular to the direction of band migration. The first nucleotide is recognized by a band in each of the three adjacent lanes. The second nucleotide is recognized by bands in the left and central lane only. The third nucleotide is recognized by bands in the center and right lanes only. (It is, of course, recognized that the left and right lanes are interchangeable and are used herein for purposes of simplifying description only.) The fourth nucleotide is recognized by a band in the center lane only.

The preferred method of reading the gel is to first read the left lane relative to the center lane and then read the right lane relative to the center lane and then to assemble the data to discern the three-band pattern. That is, at each position of the nucleotide chain ladder, as defined by the center lane, reading of each of the other lanes is reduced to a + or − reading. In assembling the data, +,+ is interpreted as the first nucleotide; +,− is interpreted as the second nucleotide; −,+ is interpreted as the third nucleotide and −,− is interpreted as the fourth nucleotide.

For manual reading of a gel, this system provides at least two advantages. First of all, the reader of the gel need only record his observations, waiting to make his evaluation until he has read and tabulated all of the data. Even though interpretation of a band pattern system is simple, even with a four band pattern system, it is found that errors frequently arise, probably due to the tedium of reading the multiplicity of band patterns. Errors of this nature are substantially reduced when there is no need to make an interpretation while reading. Secondly, reading is much easier; the technician need only determine whether a band exists in the lane adjacent to a band in the center, fully stepped lane. There is no need to track across several lanes, some of which will be blank, and make a judgment that the several bands are indeed in linear, cross-direction alignment. This is especially important when substantial bowing has occurred in the band pattern.

For automatic sequencing, a major advantage of this system is that any effect of band bowing can be substantially ignored. Even if substantial bowing has occurred, the ends of adjacent bands should be substantially aligned and easily recognized as aligned by optical scanning apparatus. The scanning apparatus need only scan the center lane for each next step and then scan the adjacent lane for the presence or absence of a band and record the presence or absence of the band as + or −. The process is repeated, comparing the other flanking band with the center band and recording the results as + or −. With this system, there is no need to compare the left and right lanes directly; thus, even if bowing of the gel causes the left- and right-hand lanes to be misaligned, the gel will not be misread, as the scanner can be adjusted to compare only the location of the ends of the adjacent gels.

It may be noted that the proposed three-lane system is not the only three-lane system that will sequence a nucleotide chain. As noted above, Maxam and Gilbert recognized that three lanes, each with a cleavage site at a first, a second, and a third of the four nucleotide sites would provide the requisite information. Similarly, three sets of two termination sites or three sets of three termination sites would each give unique band patterns across the gel for each nucleotide, site. However, the particular band pattern which is the subject of the invention is the only band pattern in which one of the lanes, i.e., the center lane, contains each step of the ladder against which the presence or absence of bands in adjacent lanes may be directly compared.

It may also be noted that the system provides sequencing regardless of which is considered the first, second, third and fourth nucleotide in this system. In chain elongation procedures, therefore, any combination of gel application chain mixtures that provides the three-band pattern is appropriate.

In accordance with a preferred aspect of the invention, the three nucleotide chain mixtures which are run in side-by-side lanes on an electrophoresis gel are provided by appropriately mixing aliquots of four nucleotide chain samples resulting from separate reactions that each generate chain fragments terminating at sites of a different specific nucleotide. The mixture which is to run as the center lane is provided by mixing aliquots of each of four samples, each providing chains terminated at sites of a different nucleotide. The mixtures which are to run as the flanking lanes are provided by mixing aliquots from a selected first and second sample and from a selected first and third sample.

An important advantage of preparing the gel application mixtures by mixing four separate reaction samples, each representing sites of a different individual nucleotide, is that by adding similar aliquots of the reaction samples to each gel application mixture (and by appropriately diluting the mixtures to provide similar volumes), the band intensities in each of the flanking lanes is substantially identical to the intensities of the bands in the center lane. Frequently electrophoresis gels of nucleotide chains are plagued by "ghost" bands which can cause confusion and misreading of a gel. By mixing aliquots of the samples so that the intensities of each of the true bands at any position in each of the three lanes are substantially identical, ghost bands can generally be eliminated from consideration. For example, assuming ghost bands to be no more than about 20% of the intensity of a true band, a scanner may be programmed to accept a flanking lane band having an intensity of 80% or more of the intensity of the band in the center lane, to ignore a flanking lane band having an intensity of 20% or less than of the corresponding band in the center lane and to call into question any band having an intensity ranging from 20% to 80% of the corresponding band in the center lane.

Because of the desirability of providing mixtures of four separate samples with chains terminating at sites of a particular nucleotide, chain termination procedures are preferred to chain cleavage or fragmentation procedures. A practical limitation to chain cleavage procedures by present day procedures is that there does not exist a full complement of reaction mixtures for efficiently and selectively cleaving at each of the four individual nucleotide sites. Rather, the presently known cleavage sequencing procedures rely on combinations of reactions that selectively cleave either at certain ones of the four nucleotide sites and also at certain pairs of the four nucleotide sites. Furthermore, those reactions which cleave at pairs of the nucleotides sites generally do not cleave equally at the sites of each member of the pair. Nevertheless, by appropriate mixing of known reaction samples, the chain cleavage procedures are adaptable to running on the three-lane pattern, affording the advantage of direct comparison of flanking lanes with a fully stepped center lane. As reaction procedures are developed for cleaving selectively at each of the four sites, the advantages of equal band intensities will be afforded to a three-band pattern gel using mixtures of aliquots from four separate cleavage reactions.

The improvement of the present invention is generally applicable to DNA sequencing methods based upon generation of chain fragments terminating at specific nucleotides. The improvement of the present invention is described herein primarily with reference to improvements of the methods of Sanger et al., Maat and Smith, and Maxam and Gilbert, as discussed above. However, it is to be understood that the improvement is applicable to other techniques in which a corresponding three-band pattern can be generated or to variations of the above-mentioned procedures.

One embodiment of the present invention involves the synthesis of a radioactive complementary copy of a single-stranded target sequence with a DNA polymerase, using the directly adjacent annealed strand of a restriction fragment as a primer. Four separate reaction mixtures each contain the four deoxynucleoside triphosphates (dNTPs), at least one of which is alpha-$^{32}$P-labelled or $^{35}$S-labelled, and each mixture also contains one of the four corresponding ddNTPs or other nucleotide analogs which serve as substrates for the polymerase but terminate further chain elongation. The reaction mixtures each generate a mixture of oligonucleotides, all with a common 5' end, but with 3' ends terminating at each site where the particular nucleotide occurs to which the ddNTP corresponds. Mixtures for electrophoresis are prepared by mixing equal aliquots of the appropriate reaction samples. The center lane mixture is prepared for gel application by mixing equal aliquots from each of the four reaction samples. The flanking lane mixtures are prepared by mixing like aliquots of selected first and second and selected first and third reaction samples along with double aliquots of diluent to equal the volume of the center lane mixture. Equal aliquots of each of these three nucleotide chain mixtures are run side-by-side on a gel electrophoresis, and the three-band pattern according to the present invention is seen.

In another embodiment of the present invention, a 5'$^{32}$P-labelled double-stranded DNA fragment is incubated in the presence of DNA polymerase I and pancreatic DNAase I in four separate reactions. Each reaction contains all four dNTPs and one of the four corresponding ddNTPs (or other chain-terminating nucleotide analog).

The pancreatic DNAase I introduces nicks, the 3' hydroxyls of which serve as priming points for DNA polymerase I. Chain extension then proceeds from the 3' end of every nick, leading to a base-specific chain termination in each reaction. The products of the reactions are fractionated on three lanes of a denaturing polyacrylamide slab gel, resolving the oligonucleotides with the common labelled 5' end.

Although the nicking and subsequent chain extension occurs on both strands, because only one is labelled, a pattern of radioactive bands is produced for only that strand, allowing its sequence to be deduced. Nicking of the fragment by DNAase I does not occur at every residue along its length, but the fact that both deoxy- and dideoxy- NTPs are present in each reaction ensures that chain extension continues through several residues of the same base from the site of the nick. Every residue in the sequence, therefore, gives rise to a band. With aliquots of the four reaction samples mixed as above, the three-band pattern of the present invention is seen or gel electrophoresis.

In each of the above-described chain elongation methods, it is understood that the fragment mixtures for the three lanes can be generated in alternate manner. For example, in either case, three reaction mixtures, one containing all four ddNTPs and the others containing first and second and first and third ddNTPs can be directly electrophoresed on a gel. This procedure modification reduces the number of reaction mixtures, but it is not preferred because it does not provide uniform band intensities from lane to lane.

In another embodiment of the present invention, fragments are produced by chain cleavage rather than by elongation. The procedure for sequencing is as follows. A double-stranded DNA chain is obtained, typically by cutting a longer chain with a restriction enzyme. For sequencing, the chain should be cut to lengths of about 500 nucleotides or less. Next, the cut chain is labeled at either the 3' end or the 5' end, typically with a radioactive tag, such as a phosphate moiety with $^{32}$P. This results in a doubly labeled, double-stranded DNA chain. At this time, the molecule may be denatured and the strands separated on a gel according to the method of Hayward, G. S., *Viroloqy* 49, 342–344 (1972) for subsequent sequencing of the strands. As this technique provides two complementary single strands, each tagged, both can be sequenced to provide a check on the sequencing of the other.

Alternatively, the strand may be further cut with a restriction enzyme that cuts at a single site to produce different sized fragments, the two fragments resolved on polyacrylamide gel, and the fragments each denatured for further sequencing. This strategy does not require resolution of the denatured single strands, as fragments of the unlabeled complementary strand portion will not be detectable.

Subsequently, the labeled, single-stranded DNA is divided into aliquots for the fragmentation reactions. The conditions of the fragmentation reactions are adjusted so that, on the average, the chain is randomly fragmented a single time and at the nucleotides containing the bases to which the particular reaction mixture specifically reacts. Several suitable reactions are described in Maxam and Gilbert, supra.

Guanine and adenine sites may be specifically cleaved by methylating these purines with dimethyl sulfate, followed by heating. The degree of relative cleavage at the A and G sites is dependent upon reaction conditions, such as acidity of the reaction mixture, and reaction conditions can be appropriately adjusted to generally equalize A and G site cleavage. An alternative A plus G cleavage using diethylprocarbonate is described by Krayev, A.S. *FEBS Letters* 130, 19–22 (1981)

C and T specific cleavage is effected by reaction with hydrazine to cleave the base, and subsequently, cleavage of the DNA chain with piperidine.

A and C site specific cleavage is effected by breaking the bases with strong alkali followed by cleavage of the DNA chain with piperidine.

To form the gel mixtures, three reaction mixtures may be used which cleave different pairs of bases, e.g., I) A plus G, II) A plus C, and III) C plus T. Subsequent to chain cleavage, part of the cleavage products of mixtures I and III may be mixed together to be run as the completely stepped center lane, while the cleavage products of I and II may be run as the left and right lanes. This approach requires no modification of presently available, well worked out, reaction protocols.

After the nucleotide chain fragments have been generated by any of the above-described methods, the appropriately mixed reaction samples are applied to separate wells of an electrophoresis gel, with the center well containing nucleotide chain fragments which represent all of the fragmentation steps, the gel is run in the conventional manner. Subsequently, the gel is either frozen or dried in a manner which tends to preserve the linear alignment of the bands. If, as is conventional, the tag is of the radioactive variety, the bands are visualized by autoradiography. If other means are employed to tag the terminal nucleotide, the bands will be visualized as is appropriate.

All of the sequencing methods described above have limitations with respect to the portion of a nucleotide chain that can be sequenced. Each method utilizes labeled chain fragments having a common end but terminating at various distances from the common end, depending upon the site of chain termination or chain cleavage. Generally, the sequence cannot be read immediately starting from the common end but rather is read starting from a nucleotide closely adjacent thereto, which first readable nucleotide will be considered for purposes of discussion to be the "primary" nucleotide. From there fragments up to an nth (n being measured from the primary nucleotide) are produced and readable on a gel. Depending upon the particular techniques employed, n at a maximum is about 500. The sequence of a long nucleotide chain must be sequenced as a composite of several individual sequencing experiments.

Although the invention is described as a three-lane band pattern, sequencing of a chain of any signficant length is generally accomplished on a plurality of electrophoretic gel applications in groups of three lanes. Typically the spacing of bands on the gel varies, with those fragments (shorter) which migrate first being spaced farther apart and those fragments (longer) which migrate last being spaced closer together. In order to read all sections of the gel clearly with more uniform spacing, the three mixtures are applied to the gel in grouped lanes at staggered times. The initially-applied set of three lanes is useful in reading the sequence of the longer fragments that are now spaced sufficiently far apart, while the later-applied sets of three lanes are used to read the sequence of the shorter fragments that more rapidly migrate apart.

As a means of providingan internal check, the invention also contemplates the use of a five-lane band pattern by which two independent three-lane band pattern evaluations are made. In the five-lane band pattern, the second and fourth lanes are fully stepped. The remaining three lanes each show chain termination at a different pair of nucleotide sites. For example, lane 1 may show chain termination at A and G; lane 2 may show termination at A and C; and lane 3 may show termination at C and T. After electrophoresis and visualization, the nucleotide sequence may first be read by comparing lanes 1 and 3 with lane 2 and then, independently, by comparing lanes and 5 with lane 4.

The band patterns may be read manually as noted above, and the band pattern is such that reading and interpretation are simplified so as to reduce errors. However, the main advantage of the system results when automatic computer assisted scanning apparatus is used to read the autoradiograph. Scanning apparatus may be programmed to read up the center of the band and detect each successive stepwise band of the center lane. After it has detected a band, it scans the band to an edge, e.g., the left-hand edge, and then proceeds to scan to a given lateral distance in the same direction. It notes whether or not a band is detected in the flanking lane and then, as directed by computing apparatus, returns to the center of the center lane band and proceeds to search for the next center lane band. By this process, the presence or absence of bands in the lane along one side of the center lane is detected and recorded. After completing reading of one side, the process is repeated for the other side, e.g., the right-hand side. After reading and recording the data from both of the flanking lanes, associated computing apparatus interprets the data and delivers a nucleotide sequence.

The computer-assisted scanning apparatus for reading the gels should have sufficient sophistication to eliminate obvious artifacts. For example, the spaces in the lanes between the bands will generally be darker than background, e.g., the lateral regions between and along the lanes. Such slight blurring of the lanes should be eliminated by scanning and computing apparatus which is capable of assigning the presence or absence of a band according to the darkness of the lane. It should also be capable of adjusting to various background darknesses. For example, if in substantially all positions it should detect a "band" in either of the flanking lanes, it should reread the lane with an appropriate adjustment for a darker background.

The invention will now be described in greater detail by way of specific example.

EXAMPLE

To test the method of the present invention, the single strand DNA phage M13mp19, whose sequence is already known, was sequenced. The single strand DNA was annealed to the universal primer (Biolabs, m13 primer 17-mer) and the primer was extended with the Klenow fragment of DNA polymerase I under four different conditions which varied only with respect to the presence of the dideoxy nucleotide triphosphate. In each case dATP was present as the alpha$^{35}$S-derivative.

The composition of the base-specific reaction mixtures is given in Table I below.

TABLE I

|  | mixture 1 (A) | mixture 2 (G) | mixture 3 (C) | mixture 4 (T) |
| --- | --- | --- | --- | --- |
| dCTP | 33 μM | 33 μM | 1.6 μM | 33 μM |
| dGTP | 33 μM | 1.6 μM | 33 μM | 33 μM |
| TTP | 33 μM | 33 μM | 33 μM | 1.6 μM |
| ddATP | 6.2 μM |  |  |  |
| ddCTP |  |  | 12.5 μM |  |
| ddGTP |  | 0.1 mM |  |  |
| dTTP |  |  |  | 0.4 mM |

Each mix also contained: 7 mM TRIS.HCl (pH=7.5), 7 mM MgCl$_2$, 50 mM NaCl, 6 mM dithiothentol.

After incubation at 37° C. for 15 minutes, 1 μl of a chase solution containing 100 μM each of dA, dG, dC, dT was added, and incubation was continued for a further 15 minutes at room temperature. The reaction was terminated by adding 5 μl of deionized formamide containing 10% XCFF.

Aliquots from each mixture were prepared for loading 5 side-by-side wells as given in Table II.

TABLE II

|  | well 1 | well 2 | well 3 | well 4 | well 5 |
| --- | --- | --- | --- | --- | --- |
| mixture 1 | 1 μl | 1 μl | 1 μl | 1 μl |  |
| mixture 2 | 1 μl | 1 μl |  | 1 μl |  |
| mixture 3 |  | 1 μl | 1 μl | 1 μl | 1 μl |
| mixture 4 |  | 1 μl |  | 1 μl | 1 μl |
| mixture 5 (diluent) | 2 μl |  | 2 μl |  | 2 μl |

The mixtures were heat denatured at 100° C. for 2 minutes, and 1 μl of each was applied to 6% acrylamide gel for electrophoresis.

Gels were set between 30cm and 50cm glass plates separated by 0.33 mm Whatman 3 mm chromatography paper. The loading wells were 5 mm wide and formed by sharktooth combs. The acrylamide gel solutions contained 6% acrylamide (19:1 acrylamide:bis acrylamide) and 460g urea per liter. Acrylamide gel mixes were made with 0.5 x and 2.5 x TBE (10 x TBE is 108 g of Tris, 55 g of boric acid and 9.3 g of EDTA per liter). The 2.5 x gel mix also contained 10% sucrose and bromophenol blue at 50 mg/liter. Gel mixes were not degassed.

Polymerization of acrylamide was initiated by adding 1 μl of 25% ammonium persulfate and 1 μl of N,N,N',N'-tetramethylethelenediamine per ml of gel mix. Immediately after adding the polymerizing agents, the gradient gels were poured. The buffer in the electrode tank was 0.5x TBE. Gels were run at 1500 volts until the dye front had run 30 centimeters. After separation of the plates, the gel was fixed in 3 liters of 5% methanol and 5 % acetic acid (vol/vol) for 15 min. Gels were then transferred to Whatman 3 mm chromatography paper, covered with Saran Wrap and the top 10 centimeters were cut away. Gels were dried for 25 min. on a gel dryer at 80° C, the Saran Wrap removed, and the gels were autoradiographed overnight at room temperature without intensifying screens.

The gels were then read in the following manner. At each ladder position, the strength of bands in lanes 1, 3 and 5 were first compared with those in 2 and 4. In every case, any band appearing in any of lanes 1, 3 or 5 had approximately the same intensity as the band in lanes 2 and 4.

Next the sequences were read by comparing the pattern of bands 1-3, and an interpretation of nucleotide position was made according to Table IIIA.

TABLE IIIA

|   | Lane 1 | Lane 2 | Lane 3 |
|---|--------|--------|--------|
| A | +      | +      | +      |
| G | +      | +      | −      |
| C | −      | +      | +      |
| T | −      | +      | −      |

Then the sequence was reread from the pattern of bands 3-5, and an independent interpretation of nucleotide position was made according to Table IIIB.

TABLE IIIB

|   | Lane 3 | Lane 4 | Lane 5 |
|---|--------|--------|--------|
| A | +      | +      | −      |
| G | −      | +      | −      |
| C | +      | +      | +      |
| T | −      | +      | +      |

Proceeding in this manner, a nucleotide sequence for the DNA was obtained first from bands 1-3 and then from bands 3-5. The sequence from each set of bands agreed completely with each other and also with the published sequence Reading was easy and unambiguous.

While the invention has been described in terms of certain particularly preferred embodiments, modifications obvious to one with ordinary skill in the art may be made without departing from the scope of the present invention. For example, although the invention has been described and exemplified with reference to reading a DNA nucleotide sequence, the three-band pattern, described herein, is equally applicable to RNA sequencing. Obvious modification of RNA sequencing according to methods, such as those described by J. M. D'Alessio, *Gel Electrophoresis of Nucleic Acids,* R. Rickwood & B. D. Hames eds., IRL Press, Oxford (1982) pp. 173-197, to produce a three-band pattern with a center, fully stepped lane, a left-hand lane with first and second nucleotide terminations and a right-hand lane with first and third nucleotide terminations.

The chain fragment mixture which is run as the center lane an electrophoretic gel contains fragments of the sequence being examined. The center lane; however, which is fully stepped, could be chain fragments of any nucleotide chain of appropriate length or even a mixture of synthetic polynucleotide chains of various length. Accordingly the center lane could be a standard chain fragment mixture which was previously prepared, e.g., commercially.

Various features of the invention are set forth in the following claims.

What is claimed is:

1. A method for sequencing a portion of a nucleotide chain from a primary nucleotide to an nth nucleotide, where n is an integer not greater than about 500, said method comprising:
    preparing a first mixture of labeled nucleotide chain fragments, each labeled chain extending from a common end adjacent to said primary nucleotide and extending to a nucleotide at a site ranging from said primary through said nth nucleotide, said first mixture containing labeled fragments of all lengths from that terminating at said primary nucleotide to that terminating at said nth nucleotide;
    preparing a second mixture of labeled nucleotide chain fragments, the labeled chain fragments extending from said common end and terminating at each position from said primary nucleotide through said nth nucleotide wherever a first of the four nucleotides occurs and wherever a second of the four nucleotides occurs;
    preparing a third mixture of labeled nucleotide chain fragments, the labeled chain fragments extending from said common end and terminating at each position from said primary nucleotide through said nth nucleotide wherever said first nucleotide occurs and wherever a third of the four nucleotides occurs;
    electrophoresing said mixtures of fragments on a gel that separates said fragments according to their length, said fragments being applied to said gel to run in side-by-side lanes;
    visualizing bands of labeled nucleotide fragments on said lanes of said gel; and
    reading the nucleotide sequence according to the band patterns in the direction normal to the lanes.

2. A method according to claim 1 wherein said nucleotide chain fragments are prepared in a plurality of reactions by obtaining a single-stranded nucleotide chain to be used as a template, annealing said single-stranded template nucleotide to a single-stranded primer, and producing a complementary copy of said template with a mixture that includes a polymerase, the four nucleoside triphosphates, and selected analogs which each correspond to one of the four nucleoside triphosphates and acts as a substrate for said polymerase but terminates chain elongation at the position of incorporation.

3. A method according to claim 2 wherein said mixtures each contains at least one nucleoside triphosphate labeled for visualization.

4. A method according to claim 1 wherein said nucleotide chain fragments are prepared by obtaining a double-stranded nucleotide chain, labeling said double-stranded nucleotide chain at a single 5' end, and nick-translating said labeled nucleotide chain in a plurality of reaction mixtures, each mixture including nick-translation enzymes, the four nucleoside triphosphates and selected analogs which each corresponds to one of the four nucleotides and acts as a substrate for said polymerase but terminates chain elongation at the position of incorporation.

5. A method according to claim 1 wherein said mixture of chain fragments is obtained by labeling a single-stranded nucleotide chain at one end, and in a plurality of reaction mixtures, cleaving aliquots of said labeled chain under conditions which cleave the same on the average of once each chain at specific ones of the four nucleotides.

6. A method according to claim 1 wherein said first mixture is applied to run in a first lane, said first lane flanked on one side by a second land to which said second mixture is applied and on the other side by a third lane to which said third mixture is applied.

7. A method according to claim 1 wherein four samples are prepared, each containing labeled nucleotide chain fragments terminating at the site of a different one of the four nucleotides and preparing said first, second and third mixtures from aliquots of said four samples.

8. A method according to claim 4 wherein four samples are prepared, each containing labeled nucleotide chain fragments terminating at the site of a different one of the four nucleotides and preparing said first, second and third mixtures from aliquots of said four samples.

9. A method according to claim 5 wherein four samples are prepared, each containing labeled nucleotide chain fragments terminating at the site of the different one of the four nucleotides and preparing said first, second and third mixtures from aliquots of said four samples.

10. A method according to claim 2 wherein said first mixture is applied to run in a first lane, said first lane flanked on one side by a second lane to which said second mixture is applied and on the other side by a third lane to which said third mixture is applied.

11. A method according to claim 3 wherein said first mixture is applied to run in a first lane, said first lane flanked on one side by a second lane to which said second mixture is applied and on the other side by a third lane to which said third mixture is applied.

12. A method according to claim 4 wherein said first mixture is applied to run in a first lane, said first lane flanked on one side by a second lane to which said second mixture is applied and on the other side by a third lane to which said third mixture is applied.

13. A method according to claim 5 wherein said first mixture is applied to run in a first lane, said first lane flanked on one side by a second lane to which said second mixture is applied and on the other side by a third lane to which said third mixture is applied.

14. A method according to claim 7 wherein said first mixture is applied to run in a first lane, said first lane flanked on one side by a second lane to which said second mixture is applied and on the other side by a third lane to which said third mixture is applied.

15. A method according to claim 2 wherein four samples are prepared, each containing labeled nucleotide chain fragments terminating at the site of a different one of the four nucleotides and preparing said first, second and third mixtures from aliquots of said four samples.

16. A method according to claim 3 wherein four samples are prepared, each containing labeled nucleotide chain fragments terminating at the site of a different one of the four nucleotides and preparing said first, second and third mixtures from aliquots of said four samples.

* * * * *

UNITED STATES PATENT AND TRADEMARK OFFICE
CERTIFICATE OF CORRECTION

PATENT NO. : 4,865,968
DATED : September 12, 1989
INVENTOR(S) : Leslie E. Orgel

It is certified that error appears in the above-identified patent and that said Letters Patent is hereby corrected as shown below:

| | |
|---|---|
| Column 1, Line 9: | After the first paragraph, and before the BACKGROUND OF THE INVENTION, insert the following paragraph: --The present invention relates to simplified DNA sequencing.--. |
| Column 9, Line 31: | Between "lanes" and "and" insert --3--. |
| Column 12, Line 59: | Change "nucleotides" to --nucleoside triphosphates--. |
| Column 13, Line 3: | Change "land" to --lane--. |
| Column 13, Line 18: | Change "the" to --a--. (2nd occurrence) |

Signed and Sealed this

Thirteenth Day of November, 1990

*Attest:*

HARRY F. MANBECK, JR.

*Attesting Officer*  *Commissioner of Patents and Trademarks*